(12) United States Patent
Kim et al.

(10) Patent No.: US 9,388,150 B2
(45) Date of Patent: Jul. 12, 2016

(54) METHOD FOR PREPARING 5-ACETOXYMETHYLFURFURAL USING ALKYLAMMONIUM ACETATE

(71) Applicants: KOREA INSTITUTE OF INDUSTRIAL TECHNOLOGY, Cheonan-si, Chungcheongnam-do (KR); SNU R&DB FOUNDATION, Gwanak-gu, Seoul (KR)

(72) Inventors: Baek Jin Kim, Cheonan-si (KR); Jin Ku Cho, Yongin-si (KR); Sangyong Kim, Cheonan-si (KR); Do Hoon Lee, Seoul (KR); Young Gyu Kim, Gunpo-si (KR); Eun-Sil Kang, Seoul (KR); Yeon-Woo Hong, Seongnam-si (KR); Da Won Chae, Seoul (KR)

(73) Assignees: KOREA INSTITUTE OF INDUSTRIAL TECHNOLOGY, Cheonan-Si (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 17 days.

(21) Appl. No.: 14/385,919

(22) PCT Filed: Mar. 15, 2013

(86) PCT No.: PCT/KR2013/002081
§ 371 (c)(1),
(2) Date: Sep. 17, 2014

(87) PCT Pub. No.: WO2013/141523
PCT Pub. Date: Sep. 26, 2013

(65) Prior Publication Data
US 2015/0051413 A1      Feb. 19, 2015

(30) Foreign Application Priority Data

Mar. 18, 2012   (KR) .................. 10-2012-0027445

(51) Int. Cl.
*C07D 307/48*      (2006.01)
*C07D 307/50*      (2006.01)

(52) U.S. Cl.
CPC ............ *C07D 307/50* (2013.01); *C07D 307/48* (2013.01)

(58) Field of Classification Search
CPC ........................... C07D 307/48; C07D 307/50
USPC .................................................. 549/483, 498
See application file for complete search history.

(56) References Cited

U.S. PATENT DOCUMENTS

2008/0221205 A1    9/2008   Kim

FOREIGN PATENT DOCUMENTS

| EP | 0044186 A1 | 1/1982 |
| JP | 53-105472 A | 9/1978 |
| WO | WO2007-104515 A1 | 9/2007 |

OTHER PUBLICATIONS

International Search Report dated Jun. 28, 2013.

*Primary Examiner* — Erich A Leeser
(74) *Attorney, Agent, or Firm* — Lucas & Mercanti, LLP; Yun H. Choe

(57) ABSTRACT

The present invention relates to a method for preparing 5-acetoxymethylfurfural, comprising a step of synthesizing 5-acetoxymethylfurfural by reacting 5-halomethyl furfural with alkylammonium acetate. The present invention can provide a method for preparing 5-acetoxymethylfurfural which is economic and has high reaction efficiency even without using an additional base.

10 Claims, No Drawings

METHOD FOR PREPARING 5-ACETOXYMETHYLFURFURAL USING ALKYLAMMONIUM ACETATE

CROSS-REFERENCE TO RELATED APPLICATIONS

This application is a 371 of PCT/KR2013/002081, filed Mar. 15, 2013, which claims the benefit of Korean Patent Application No. 10-2012-0027445, filed Mar. 18, 2012, the contents of each of which are incorporated herein by reference.

BACKGROUND OF THE INVENTION

1. Technical Field

The present invention relates to a method of preparing 5-acetoxymethylfurfural, and, more particularly, to a method of preparing 5-acetoxymethylfurfural using an alkylammonium acetate salt, which is economical and has high reaction efficiency.

2. Description of the Related Art

Due to the exhaustion of traditional energy sources together with the increase of world-wide energy demand, the development of alternative energy sources is currently receiving much attention. Among alternative energy sources, biomass has attracted considerable attention as a quantitative biological resource that can be regenerated, as shown in the alternative energy development project "Production of fuel from biomass" conducted by U.S. Department of Energy (DOE). 5-hydroxymethylfurfural (HMF) is a biomass-derived material that can replace petrochemical-based compounds whose production and usage have already been established, and, to date, research into this 5-hydroxymethylfurfural has been conducted.

It was reported that HMF is generally synthesized by the dehydration reaction of hexose in the presence of a metal catalyst. However, this synthesis method has been difficult to commercialize because of a difficulty in separation attributable to the usage of a specific reaction solvent, an anhydrous condition attributable to the usage of a metal catalyst, reduction of yield, and the like. As a method for solving the above problem, there was proposed a method of synthesizing 5-chloromethylfurfural (CMF) which is a precursor of HMF and derivatives thereof. Such synthesized products have relatively high stability and are obtained in a high yield (*Chem. Sus. Chem.* 2009, 2, 859; *Angew. Chem. Int. Ed.* 2008, 47, 7924).

5-acetoxymethylfurfural (AcHMF) is a main target material in the derivation reaction of HMF using CMF as a starting material. Since AcHMF is structurally similar to HMF, it has high reactivity, high multifunctionality and high lipophilicity and is comparatively stable, so it can replace HMF at the time of synthesis of furan-based monomers.

Meanwhile, a method of synthesizing AcHMF from 5-chloromethylfurfural (CMF) using acetic acid and inorganic bases was reported in the patent document (US2008/221205 A1). However, this method is problematic in that it has low practicality because of its low production yield.

Therefore, if an efficient AcHMF preparation method is developed, a mass-production process can be equipped based on the method and low-priced raw materials can be sufficiently supplied, therefore the demand for AcHMF as an industrial product will expand.

SUMMARY OF THE INVENTION

Accordingly, the present invention has been devised to solve the above-mentioned problems, and a first object of the present invention is to provide a method of preparing 5-acetoxymethylfurfural that can be used as a platform compound.

A second object of the present invention is to provide a method of preparing 5-acetoxymethylfurfural, which is performed by a simple process and has a high reaction yield.

A third object of the present invention is to provide a method of preparing 5-acetoxymethylfurfural, in which a biomass-derived material can be used as a reactant.

In order to accomplish the above objects, an aspect of the present invention provides a method of preparing 5-acetoxymethylfurfural, including the step of reacting 5-halomethylfurfural represented by the following Formula 1 with an alkylammonium acetate salt to synthesize 5-acetoxymethylfurfural represented by the following Formula 2:

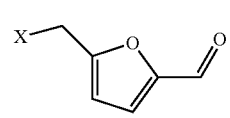

[Formula 1]

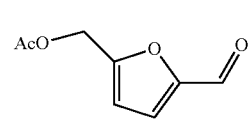

[Formula 2]

In the Formula 1, X is any one selected from among fluorine, chlorine, bromine and iodine atoms, and In the Formula 2, AcO is

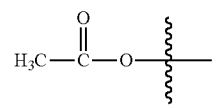

In the method, the alkylammonium acetate salt may be at least one selected from the group consisting of a primary ammonium acetate salt, a secondary ammonium acetate salt, a tertiary ammonium acetate salt and a quaternary ammonium acetate salt.

Further, the alkylammonium acetate salt is at least one selected from among alkylammonium acetate salts represented by the following Formulae 3 and 4:

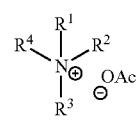

[Formula 3]

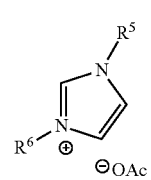

[Formula 4]

In the Formulae 3 and 4, R1 to R6 are each independently a straight-chain alkyl group of C1 to C10, a branch-chain alkyl group of C3 to C10 or a cycloalkyl group of C3 to C14, and AcO is

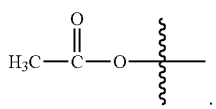

In the method, the step of synthesizing 5-acetoxymethylfurfural may be performed in a first organic solvent.

The first organic solvent may be nitrile, ether, chloroalkane, ketone and ester compound.

For example the first organic solvent may be at least one selected from the group consisting of acetonitrile, propiononitrile, adiponitrile, benzonitrile dimethyl ether, diethyl ether, dipropyl ether, dichloroethyl ether, diisopropyl ether, n-butylethyl ether, diisoamyl ether, methylphenyl ether, tetrahydrofuran, methane monochloride, methane dichloride, methane trichloride, methane tetrachloride, ethane dichloride, ethane trichloride, ethane tetrachloride, ethylene dichloride, ethylene trichloride, ethylene tetrachloride, propane dichloride, propane trichloride, acetone, methyl ethyl ketone, ethyl ethyl ketone, methyl acetate, ethyl acetate, propyl acetate and tert-butyl acetate.

The method may further include the step of separating 5-acetoxymethylfurfural of Formula 2 through extraction using a second organic solvent and water, after the step of synthesizing 5-acetoxymethylfurfural.

The second organic solvent may be at least one selected from the group consisting of diethyl ether, dichloroethyl ether, diisopropyl ether, n-butyl ether, diisoamyl ether, methylphenyl ether, tetrahydrofuran, ethyleneglycol monomethyl ether, ethyleneglycol monoethyl ether, methyl acetate, ethyl acetate, methyl cellosolve acetate, ethyl cellosolve acetate, diethyl cellosolve acetate, methylethyl carbitol, diethyl carbitol, diethyleneglycol monomethyl ether, diethyleneglycol monoethyl ether, diethyleneglycol dimethyl ether, diethyleneglycol methylethyl ether, diethyleneglycol diethyl ether, propyleneglycol methyl ether acetate, propyleneglycol propyl ether acetate, methane dichloride, methane trichloride, toluene, xylene, methyl ethyl ketone, cyclohexanone, 4-hydroxy-4-methyl-2-pentanone, methyl-n-propyl ketone, methyl-n-butyl ketone, methyl-n-amyl ketone and 2-heptanone. The amount of the alkylammonium acetate salt may be 1 to 30 parts by equivalent based on 1 part by equivalent of 5-halomethylfurfural represented by Formula 1 above.

The step of synthesizing 5-acetoxymethylfurfural is performed at a temperature of −80 to 100° C.

The step of synthesizing 5-acetoxymethylfurfural may be performed for 1 to 120 minutes.

DESCRIPTION OF THE PREFERRED EMBODIMENTS

Hereinafter, embodiments of the present invention will be described in detail such that they can be easily carried out by those skilled in the art.

The present invention may be embodied in many different forms without departing from the spirit and significant characteristics of the invention. Therefore, the embodiments of the present invention are disclosed only for illustrative purposes and should not be construed as limiting the present invention. Further, in the description of the present invention, when it is determined that the detailed description of the related art would obscure the gist of the present invention, the description thereof will be omitted.

The terms used herein are for the purpose of describing particular embodiments only and are not intended to be limiting. As used herein, the singular forms "a," "an" and "the" are intended to include the plural forms as well, unless the context clearly indicates otherwise. It will be further understood that the terms "comprise", "include", "have", etc. when used in this specification, specify the presence of stated features, integers, steps, operations, elements, components, and/or combinations of them but do not preclude the presence or addition of one or more other features, integers, steps, operations, elements, components, and/or combinations thereof.

Hereinafter, preferred embodiments of the present invention will be described in detail. These embodiments are set forth to illustrate the present invention, and the scope of the present invention is not limited thereto. The present invention is only defined by the following claims. As used herein, the term "alkyl group" is referred to as "a straight-chain, branch-chain or cyclic aliphatic hydrocarbon group," unless otherwise defined. The alkyl group may be a saturated alkyl group including no double bond and triple bond.

The alkyl group may be an unsaturated alkyl group including at least one double or triple bond.

The alkyl group may be an alkyl group of C1 to C14. More specifically, the alkyl group may be an alkyl group of C1 to C10 or C1 to C6.

For example, the alkyl group of C1 to C4 includes an alkyl chain of 1 to 4 carbon atoms, and the alkyl chain of 1 to carbon atoms is selected from the group consisting of methyl, ethyl, propyl, iso-propyl, n-butyl, iso-butyl, sec-butyl and t-butyl.

Specific examples of the alkyl group may include a methyl group, an ethyl group, a propyl group, an iso-propyl group, a butyl group, an iso-butyl group, a t-butyl group, a pentyl group, a hexyl group, an ethenyl group, a propenyl group, a butenyl group, a cyclopropyl group, a cyclobutyl group, a cyclopentyl group, a cyclohexyl group, and the like.

Preparation of 5-acetoxymethylfurfural

The present invention provides a method of preparing 5-acetoxymethylfurfural, including the step of reacting 5-halomethylfurfural represented by the following Formula 1 with an alkylammonium acetate salt to synthesize 5-acetoxymethylfurfural represented by the following Formula 2:

[Formula 1]

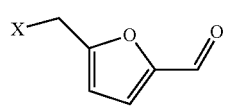

[Formula 2]

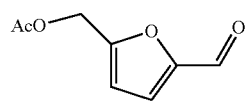

In the Formula 1, X is any one selected from among fluorine, chlorine, bromine and iodine atoms, and
In the Formula 2, AcO is

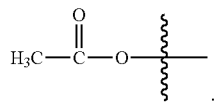

The alkylammonium acetate salt may be at least one selected from the group consisting of a primary ammonium acetate salt, a secondary ammonium acetate salt, a tertiary ammonium acetate salt and a quaternary ammonium acetate salt.

As used herein, the primary ammonium acetate salt may be a salt in which a primary ammonium ion formed by substituting one hydrogen atom of an ammonium ion ($NH_4^+$) with an alkyl group is bonded with an acetate ion.

As used herein, the secondary ammonium acetate salt may be a salt in which a secondary ammonium ion formed by substituting two hydrogen atoms of an ammonium ion ($NH_4^+$) with alkyl groups is bonded with an acetate ion, or may be a salt in which a secondary ammonium ion formed by substituting two hydrogen atoms of an ammonium ion ($NH_4^+$) with one hydrocarbon or heterohydrocarbon group including carbon double-bonded with nitrogen of the ammonium ion is bonded with an acetate ion.

As used herein, the tertiary ammonium acetate salt may be a salt in which a tertiary ammonium ion formed by substituting three hydrogen atoms of an ammonium ion ($NH_4^+$) with alkyl groups is bonded with an acetate ion, or may be a salt in which a tertiary ammonium ion formed by substituting two hydrogen atoms of an ammonium ion ($NH_4^+$) with one hydrocarbon or heterohydrocarbon group including carbon double-bonded with nitrogen of the ammonium ion and substituting one hydrogen atom thereof with an alkyl group is bonded with an acetate ion. For example, the tertiary ammonium acetate salt may be 1-ethyl-3-methylimidazolium acetate.

As used herein, the quaternary ammonium acetate salt may be a salt in which a quaternary ammonium ion formed by substituting four hydrogen atoms of an ammonium ion ($NH_4^+$) with alkyl groups is bonded with an acetate ion, or may be a salt in which a quaternary ammonium ion formed by substituting two hydrogen atoms of an ammonium ion ($NH_4^+$) with one hydrocarbon or heterohydrocarbon group including carbon double-bonded with nitrogen of the ammonium ion and substituting two hydrogen atoms thereof with alkyl groups is bonded with an acetate ion. For example, the quaternary ammonium acetate salt may be 1-ethyl-3-methylimidazolium acetate.

As used herein, the term "heterohydrocarbon" means a hydrocarbon whose one function group contains 1 to 3 heteroatoms selected from the group consisting of N, O, S and P and whose other functional groups contain C or H.

Specifically, the alkylammonium acetate salt may be at least one selected from among alkylammonium acetate salts represented by the following Formulae 3 and 4:

[Formula 3]

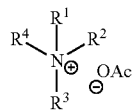

[Formula 4]

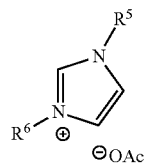

In the Formulae 3 and 4, R1 to R6 are each independently a straight-chain alkyl group of C1 to C10, a branch-chain alkyl group of C3 to C10 or a cycloalkyl group of C3 to C14, and
ACO is

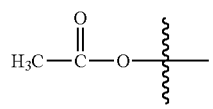

In the method, the step of synthesizing 5-acetoxymethylfurfural may be performed in a first organic solvent.

Here, the first organic solvent may be at least one selected from the group consisting of acetonitrile, propiononitrile, adiponitrile, benzonitrile, dimethyl ether, diethyl ether, dipropyl ether, dichloroethyl ether, diisopropyl ether, n-butylethyl ether, diisoamyl ether, methylphenyl ether, tetrahydrofuran, methane monochloride, methane dichloride, methane trichloride, methane tetrachloride, ethane dichloride, ethane trichloride, ethane tetrachloride, ethylene dichloride, ethylene trichloride, ethylene tetrachloride, propane dichloride, propane trichloride, acetone, methyl ethyl ketone, ethyl ethyl ketone, methyl acetate, ethyl acetate, propyl acetate and tert-butyl acetate.

The amount of the alkylammonium acetate salt may be 1 to 30 parts by equivalent based on 1 part by equivalent of 5-halomethylfurfural represented by Formula 1 above. When the amount thereof is less than 1 part by equivalent, reactants are not sufficiently reacted, thus decreasing the yield of 5-acetoxymethylfurfural, and, when the amount thereof is more than 30 parts by equivalent, economical efficiency is lowered.

The step of synthesizing 5-acetoxymethylfurfural may be performed at a temperature of −80 to 100° C., preferably, 0 to 80° C. When the synthesis reaction is performed at lower than −80° C., this reaction slowly proceeds, and, when the synthesis reaction is performed at higher than 100° C., this reaction proceeds extremely violently, thus generating by-products in large amounts.

The step of synthesizing 5-acetoxymethylfurfural may be performed for 1 to 120 minutes, preferably, 10 to 100 minutes. When the synthesis reaction time is less than 1 minute, a starting material may not be sufficiently reacted, and, when the synthesis reaction time is more than 120 minutes, the synthesis reaction may no longer proceed.

Currently, there is proposed a method of synthesizing AcHMF from halomethylfurfural using acetic acid and an inorganic base. However, this method is disadvantageous in that the yield of AcHMF is not high, thus decreasing practicality and in that a base must be additionally used.

The method of the present invention has overcome the above disadvantages by using an alkylammonium salt that can obtain a high reaction rate and a high yield.

The reaction may be performed at normal pressure or while changing pressure. In this case, it is obvious to those skilled in the art that reaction time and reaction temperature can be suitably adjusted according to the change of pressure.

Separation of 5-acetoxymethylfurfural

The method may further include the step of separating 5-acetoxymethylfurfural of Formula 2 through extraction using a second organic solvent and water, after the step of synthesizing 5-acetoxymethylfurfural. The step of separating 5-acetoxymethylfurfural using extraction is briefly described as follows. This extraction is a method of separating 5-acetoxymethylfurfural using the fact that alkylammonium halide existing as a salt is different from 5-acetoxymethylfurfural in solubility.

As the second organic solvent, various types of organic solvent may be used. However, an organic solvent having relatively high polarity may be used as the second organic solvent because 5-acetoxymethylfurfural may not be easily dissolved according to the degree of polarity of an organic solvent. Therefore, the organic solvent which can be used in the present invention may be an organic solvent that is not easily mixed with water, rather than an amine-based solvent.

Specific examples of the second organic solvent may include, but are not limited to, diethyl ether, dichloroethyl ether, diisopropyl ether, n-butyl ether, diisoamyl ether, methylphenyl ether, tetrahydrofuran, ethyleneglycol monomethyl ether, ethyleneglycol monoethyl ether, methyl acetate, ethyl acetate, methyl cellosolve acetate, ethyl cellosolve acetate, diethyl cellosolve acetate, methylethyl carbitol, diethyl carbitol, diethyleneglycol monomethyl ether, diethyleneglycol monoethyl ether, diethyleneglycol dimethyl ether, diethyleneglycol methylethyl ether, diethyleneglycol diethyl ether, propyleneglycol methyl ether acetate, propyleneglycol propyl ether acetate, methane dichloride, methane trichloride, toluene, xylene, methyl ethyl ketone, cyclohexanone, 4-hydroxy-4-methyl-2-pentanone, methyl-n-propyl ketone, methyl-n-butyl ketone, methyl-n-amyl ketone and 2-heptanone. These organic solvents may be used independently or in a mixture thereof.

The amount of the second organic solvent used in acid-base extraction may be equal to or 500 times that of water, preferably 10 to 100 times that of water. When the amount of the second organic solvent is less than that of water, it is difficult to extract 5-acetoxymethylfurfural, and, when the amount thereof is more than 100 times that of water, the extraction effect of 5-acetoxymethylfurfural may be decreased.

In the present invention, unless otherwise specified, the yield of 5-acetoxymethylfurfural is expressed by Equation 1 below:

Yield (%)=(real yield/theoretical yield)×100     [Equation 1]

Meanwhile, the present invention provides 5-acetoxymethylfurfural prepared by the method of the present invention.

Hereinafter, the present invention will be described in more detail with reference to the following Examples. However, these Examples are set forth to illustrate the present invention, and the scope of the present invention is not limited thereto.

EXAMPLES

Example 1

In a round flask, 2 mL of methyl cyanide (acetonitrile) as an organic solvent was introduced, 0.145 g (1 mmol) of 5-chloromethylfurfural (CMF, compound I) was dissolved in the organic solvent, 0.302 g (1 mmol) of tetrabutylammonium acetate was added to the solution, and then the mixed solution was reacted at normal pressure and room temperature for 5 minutes. After the reaction, the reaction product was extracted by the addition of a small amount of water (5 mL) and ethyl acetate (added twice by 20 mL) to obtain an organic layer. The obtained organic layer was concentrated under reduced pressure to obtain light yellow liquid 5-acetoxymethylfurfural (AcHMF, compound II). The yield thereof is 97%.

It was ascertained by 1H-NMR that the light yellow liquid is a target material. Analysis data is as follows.

AcHMF: 1H NMR (400 MHz, CDCl$_3$) 9.65 (s, 1H), 7.25 (d, J=3.6, 1H), 6.62 (d, J=3.6, 1H), 5.13 (s, 2H), 2.12 (s, 3H)

Example 2

In a round flask, 2 mL of methyl cyanide (acetonitrile) as an organic solvent was introduced, 0.145 g (1 mmol) of 5-chloromethylfurfural (CMF, compound I) was dissolved in the organic solvent, 0.133 g (1 mmol) of tetramethylammonium acetate was added to the solution, and then the mixed solution was reacted at normal pressure and room temperature for 5 minutes. After the reaction, the reaction product was extracted by the addition of a small amount of water (5 mL) and ethyl acetate (added twice by 20 mL) to obtain an organic layer. The obtained organic layer was concentrated under reduced pressure to obtain light yellow liquid 5-acetoxymethylfurfural (AcHMF, compound II). The yield thereof is 95%.

It was ascertained by 1H-NMR that the light yellow liquid is a target material. Analysis data is as follows.

AcHMF: 1H NMR (400 MHz, CDCl$_3$) 9.65 (s, 1H), 7.25 (d, J=3.6, 1H), 6.62 (d, J=3.6, 1H), 5.13 (s, 2H), 2.12 (s, 3H)

Example 3

In a round flask, 2 mL of methyl cyanide (acetonitrile) as an organic solvent was introduced, 0.145 g (1 mmol) of 5-chloromethylfurfural (CMF, compound I) was dissolved in the organic solvent, 0.170 g (1 mmol) of 1-ethyl-3-methylimidazolium acetate was added to the solution, and then the mixed solution was reacted at normal pressure and room temperature for 5 minutes. After the reaction, the reaction product was extracted by the addition of a small amount of water (5 mL) and ethyl acetate (added twice by 20 mL) to obtain an organic layer. The obtained organic layer was concentrated under reduced pressure to obtain light yellow liquid 5-acetoxymethylfurfural (AcHMF, compound II). The yield thereof is 36%.

It was ascertained by 1H-NMR that the light yellow liquid is a target material. Analysis data is as follows.

AcHMF: 1H NMR (400 MHz, CDCl3) 9.65 (s, 1H), 7.25 (d, J=3.6, 1H), 6.62 (d, J=3.6, 1H), 5.13 (s, 2H), 2.12 (s, 3H)

Comparative Example 1

In a round flask, 2 mL of methyl cyanide (acetonitrile) as an organic solvent was introduced, 0.145 g (1 mmol) of 5-chloromethylfurfural (CMF, compound I) was dissolved in the organic solvent, 0.077 g (1 mmol) of ammonium acetate was added to the solution, and then the mixed solution was reacted at normal pressure and room temperature. When the progress of the reaction was observed by thin-film chromatography a reaction product was not discovered. For analysis, the reacted mixed solution was extracted by the addition of a small amount of water (5 mL) and ethyl acetate (added twice by 20 mL) to obtain an organic layer. The obtained organic layer was concentrated under reduced pressure, but light yellow liquid 5-acetoxymethylfurfural (AcHMF, compound II) was not obtained, and only the 5-chloromethylfurfural as a starting material was recovered.

Nuclear Magnetic Resonance Analysis

The nuclear magnetic resonance analysis of the reaction products was conducted using AVIII400 (1H-400 MHz, manufactured by Bruker Corporation) after dissolving each of the reaction products in deuterated chloroform ($CDCl_3$) containing 0.05% of tetramethyl silane (TMS) as an internal standard material.

As described above, in the present invention, according to the reaction using an alkylammonium acetate salt, high value-added AcHMF can be rapidly obtained at high yield. The reason for this is inferred that, when an alkylammonium acetate salt having high solubility in an organic solvent is used as a nucleophile, the reaction rate becomes high, and AcHMF is easily extracted because of its high lipophilicity.

According to the method of the present invention, 5-acetoxymethylfurfural used as a platform compound such as HMF or the like can be prepared.

Further, according to the method of the present invention, 5-acetoxymethylfurfural can be prepared at a high reaction yield through a simple process without using a base.

Further, according to the method of the present invention, a biomass-derived material can be used as a reactant.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

Accordingly, any and all modifications, variations or equivalent arrangements should be considered to be within the scope of the invention, and the detailed scope of the invention will be disclosed by the accompanying claims.

What is claimed is:

1. A method of preparing 5-acetoxymethylfurfural comprising:
    reacting 5-halomethylfurfural represented by the following Formula 1 with an alkylammonium acetate salt to synthesize 5-acetoxymethylfurfural represented by the following Formula 2:

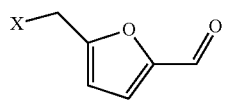

[Formula 1]

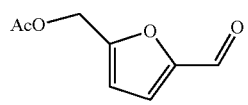

[Formula 2]

wherein X is fluorine, chlorine, bromine or iodine, and AcO is

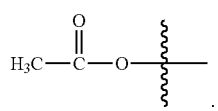

2. The method of claim 1, wherein the alkylammonium acetate salt is a primary ammonium acetate salt, a secondary ammonium acetate salt, a tertiary ammonium acetate salt or a quaternary ammonium acetate salt.

3. The method of claim 1, wherein the alkylammonium acetate salt is an alkylammonium acetate salt represented by the following Formulae 3 or 4:

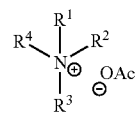

[Formula 3]

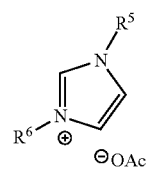

[Formula 4]

wherein $R^1$ to $R^6$ are each independently a straight-chain alkyl group of C1 to C10, a branch-chain alkyl group of C3 to C10 or a cycloalkyl group of C3 to C14.

4. The method of claim 1, wherein the step of synthesizing 5-acetoxymethylfurfural is performed in a first organic solvent.

5. The method of claim 4, wherein the first organic solvent is at least one selected from the group consisting of acetonitrile, propiononitrile, adiponitrile, benzonitrile dimethyl ether, diethyl ether, dipropyl ether, dichloroethyl ether, diisopropyl ether, n-butylethyl ether, diisoamyl ether, methylphenyl ether, tetrahydrofuran, methane monochloride, methane dichloride, methane trichloride, methane tetrachloride, ethane dichloride, ethane trichloride, ethane tetrachloride, ethylene dichloride, ethylene trichloride, ethylene tetrachloride, propane dichloride, propane trichloride, acetone, methyl ethyl ketone, ethyl ethyl ketone, methyl acetate, ethyl acetate, propyl acetate and tert-butyl acetate.

6. The method of claim 1, further comprising the step of separating 5-acetoxymethylfurfural of Formula 2 through extraction using a second organic solvent and water, after the step of synthesizing 5-acetoxymethylfurfural.

7. The method of claim 6, wherein the second organic solvent is at least one selected from the group consisting of diethyl ether, dichloroethyl ether, diisopropyl ether, n-butyl ether, diisoamyl ether, methylphenyl ether, tetrahydrofuran, ethyleneglycol monomethyl ether, ethyleneglycol monoethyl ether, methyl acetate, ethyl acetate, methyl cellosolve acetate, ethyl cellosolve acetate, diethyl cellosolve acetate, methylethyl carbitol, diethyl carbitol, diethyleneglycol monomethyl ether, diethyleneglycol monoethyl ether, diethyleneglycol dimethyl ether, diethyleneglycol methylethyl ether, diethyleneglycol diethyl ether, propyleneglycol methyl ether acetate, propyleneglycol propyl ether acetate, methane dichloride, methane trichloride, toluene, xylene, methyl ethyl ketone, cyclohexanone, 4-hydroxy-4-methyl-2-pentanone, methyl-n-propyl ketone, methyl-n-butyl ketone, methyl-n-amyl ketone and 2-heptanone.

8. The method of claim 1, wherein an amount of the alkylammonium acetate salt is 1 to 30 parts by equivalent based on 1 part by equivalent of 5-halomethylfurfural represented by Formula 1 above.

9. The method of claim 1, wherein the step of synthesizing 5-acetoxymethylfurfural is performed at a temperature of −80 to 100° C.

10. The method of claim 1, wherein the step of synthesizing 5-acetoxymethylfurfural is performed for 1 to 120 minutes.

* * * * *